United States Patent [19]

Kirsch et al.

[11] Patent Number: 4,950,281
[45] Date of Patent: Aug. 21, 1990

[54] EVERTING FORCEPS

[75] Inventors: Wolff M. Kirsch; Yong H. Zhu, both of Albuquerque; Robert Cushman, Cedar Crest, all of N. Mex.

[73] Assignee: University of New Mexico, Albuquerque, N. Mex.

[21] Appl. No.: 309,372

[22] Filed: Feb. 13, 1989

[51] Int. Cl.5 .............................................. A61B 17/28
[52] U.S. Cl. ................................... 606/207; 294/99.2; 81/424.5
[58] Field of Search ............................... 128/321–326, 128/354; 294/99.2; 433/154; 81/424.5, 426, 426.5; 606/205–207, 210

[56] References Cited

U.S. PATENT DOCUMENTS

| 99,050 | 1/1870 | Battle | 433/154 |
| 781,277 | 10/1904 | Fahey | 433/154 |
| 2,214,984 | 9/1940 | Bachmann | |
| 4,024,870 | 5/1977 | Sandel | 81/424.5 |
| 4,192,204 | 3/1980 | Feldman | 294/1.2 |
| 4,192,313 | 3/1980 | Ogami | 81/424.5 |

FOREIGN PATENT DOCUMENTS

| 0580017 | 10/1924 | France | 128/355 |
| 0762879 | 9/1980 | U.S.S.R. | 128/346 |

Primary Examiner—C. Fred Rosenbaum
Assistant Examiner—William W. Lewis
Attorney, Agent, or Firm—Charles Fallow; Martin Hoffman

[57] ABSTRACT

A forceps for holding and everting vessels in an anastomosis procedure includes three cooperating jaws mounted at the ends of respective relatively movable legs. The legs can be independently manipulated in order to secure and evert first one vessel, then another in apposition to the first, so that clips or sutures can be applied to complete the anastomosis.

9 Claims, 2 Drawing Sheets

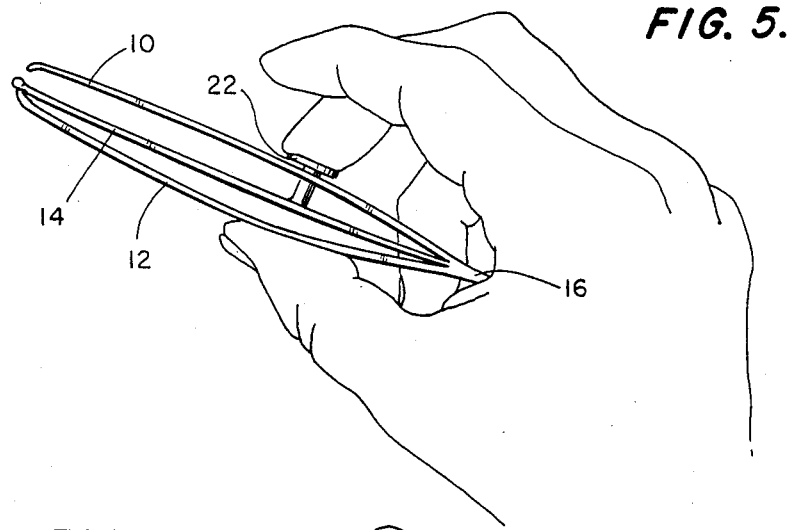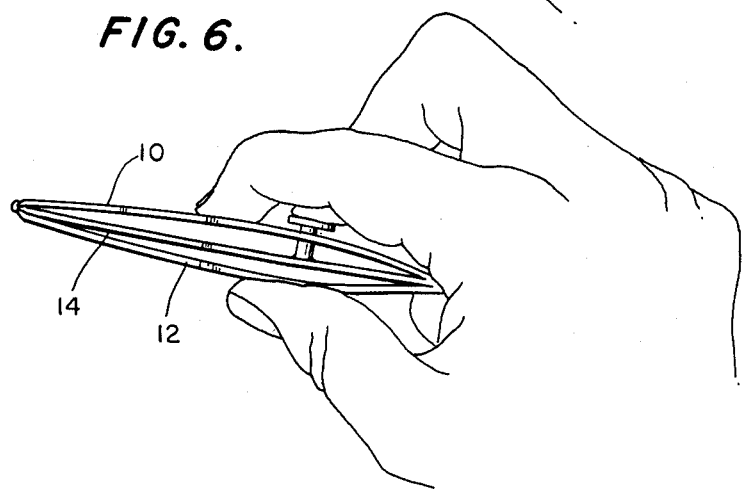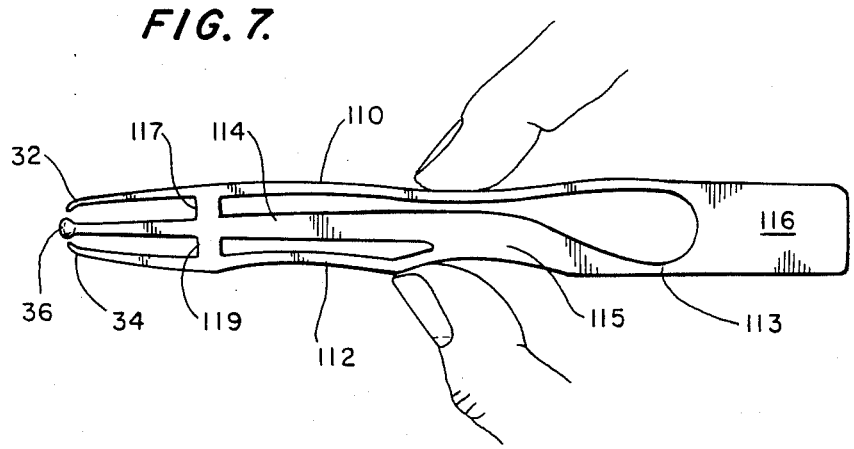

EVERTING FORCEPS

BACKGROUND

This invention relates to the field of surgery and more particularly to a tool useful for performing anastomoses and skin closures.

The term "anastomosis" covers a variety of procedures in which blood vessels or other tubular members, such as parts of the colon, are joined or reconnected. Vessels may be joined in a variety of relative orientations, including end-to-side, and end-to-end. Solid tubular structures such as peripheral nerves can also be joined together, as well as solid structures such as subcutaneous tissue and skin.

Anastomoses are traditionally performed by suturing the vessels together at the juncture between them. Alternatives to suturing have been developed, in order to prevent thrombosis which tends to occur at the points of penetration of the sutures. One such alternative, particularly for larger vessels, involves mechanical connectors such as collars. A second alternative is the use of surgical clips which are applied along the vessel juncture to perform a holding function similar to that of sutures, without penetrating the vessel walls. Two such clips, developed by the present inventors, are shown in U.S. Pat. Nos. 4,586,503 and 4,733,660. As described in the former patent, the clips are applied over apposed edges of the vessels, the edges first being everted (turned outward) to form flanges that are gripped between the jaws of the clips. Eversion not only gives the clip jaws a better purchase on the vessels, but also insures that only the interior surfaces of the vessels are in contact.

The use of non-penetrating clips requires that the vessel or tissue edges be accurately and symmetrically everted. Correct eversion is critical at the beginning of anastomoses and at difficult sites, such as at the heel and toe of an end-to-side anastomosis.

Proper eversion is difficult to achieve, since the tension along the periphery of the flange creates an unstable situation between lower-stress alternatives of the original uneverted configuration and a configuration in which the flange folds back over the vessel to form a cuff. The fact that surgical clips have proven fast, simple to apply and reliable in their holding ability, has accentuated the need for a tool to assist a surgeon in everting vessels while performing anastomoses.

Clips are typically applied with a small hand-held tool that enables the surgeon to place precisely the clip over the tissue edges, and then to close the clip, as by applying a squeezing pressure to the tool. It is desirable to enable the same surgeon to perform the required vessel eversion, with his free hand.

SUMMARY OF THE INVENTION

It is therefore an object of the invention to provide a surgical tool operable with one hand, specifically designed to evert the edges of vessels during an anastomosis, and to hold them in apposition for clipping or suturing. It is a further object to render such a tool small, of simple manufacture, and easy to clean and sterilize. Another object is to avoid any damage to the vessels being joined, since the invention is particularly intended for use with microsurgical clips designed to avoid doing puncture-type injury themselves.

In view of the foregoing, the invention is embodied in an everting forceps, comprising a pair of outer, resilient legs rigidly interconnected at one end thereof, a third leg intermediate the pair of legs, the outer and intermediate legs having respective tips at their free ends, the tips being provided with respective jaws, and further comprising externally manipulable means connected to the intermediate leg for enabling one to move the intermediate leg with respect to one of the outer legs.

BRIEF DESCRIPTION OF THE DRAWINGS

In the accompanying drawings,

FIGS. 5 and 6 show the tool in the hand of a surgeon; and

FIG. 7 is a side elevation of a second embodiment of the invention.

DESCRIPTION OF THE PREFERRED EMBODIMENT

Figure 1:
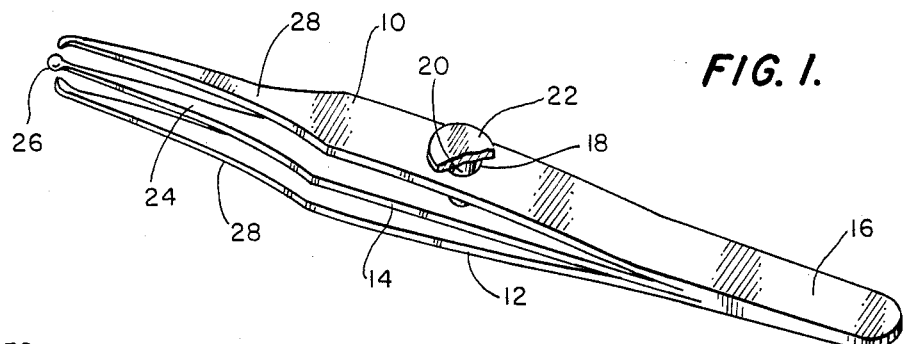
FIG. 1 is a side elevation of a tool embodying the invention.
Figure 2:
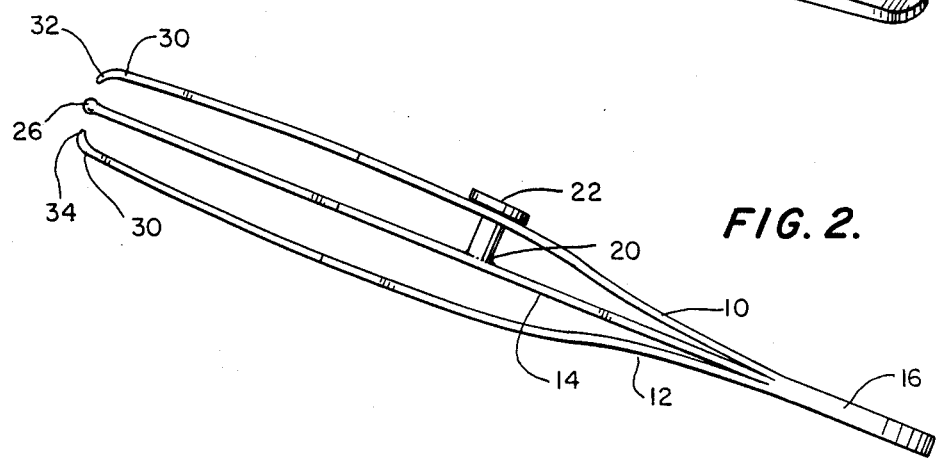
FIG. 2 is a perspective view thereof.

FIGS. 1 and 2 show an everting forceps embodying the invention. The forceps includes three legs 10, 12, 14 of spring metal or other suitable resilient material, interconnected in laminar fashion at one end as by welding or soldering to form a head 16. For convenience, the outer legs 10 and 12 are referred to as the upper and lower legs, respectively, according to their position in FIG. 1, although no particular orientation of the tool is required in use.

Figure 3:
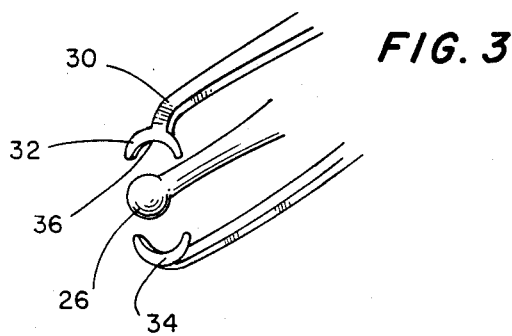
FIG. 3 is a detailed perspective view of the jaws thereof.

The intermediate leg 12 is substantially planar, and extends between the upper and lower legs 10 and 14, both of which are bowed outwardly along their unconnected portions, away from the intermediate leg. The upper leg 10 has an aperture 18 near its midpoint, through which a small transverse shaft 20, welded to the intermediate leg, extends. The shaft has a button end 22 affixed thereon outside of the upper leg, which serves as externally manipulable means that enables the surgeon to control the position of the inner leg, as described hereafter. The free end of the inner leg tapers towards a tip having a preferably spherical jaw, as shown in detail in FIG. 3; however, the shape of the jaw may be modified as desired for particular applications.

The upper and lower legs 10, 14 have similarly tapered free ends 28, which are bent inwardly near their ends at 30 and terminate at similar jaws 32, 34 facing one another opposite the tip of the intermediate leg. Each of the jaws is substantially C-shaped, when viewed from the end thereof, the inner surface 36 of each jaw having a radius of curvature slightly greater than that of the spherical tip 26. Each of the jaws may be coated with a plastic material to soften the clamping surfaces.

The three jaws normally are maintained spaced apart from one another, with the intermediate jaw centered between the arcuate jaws, by the natural resilience of the legs, thus providing a bias against any squeezing action applied by the surgeon.

Figure 4:
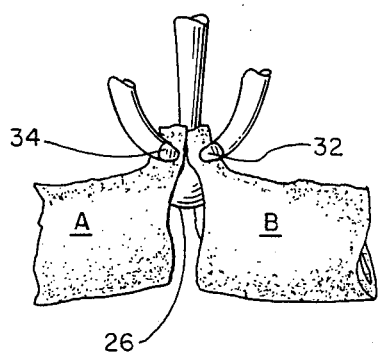
FIG. 4 shows the tool in use during an anastomosis.

In a typical anastomosis operation, as shown in FIG. 4, two approximated vessel ends A, B are ready to be joined while held in position by the everting forceps. It is preferred that the tool be held as shown in FIG. 5, that is, with the thumb on the lower leg 14, the middle finger on the button 22, and the index finger on the upper leg, the tool head 16 being steadied by the palm of the hand.

By positioning the spherical jaw 26 within the vessel lumen and the lower jaw 34 against the outside of the vessel A and then applying pressure first between the thumb and middle finger tip, the surgeon grasps and partially everts the vessel. Then, while still grasping the first vessel, the jaw 26 is inserted into the lumen vessel B, with the jaw 32 on the outside of the vessel. By applying pressure to the outer surface of the leg 10 with the index finger, the surgeon grasps the second vessel edge, similarly everting it, and holding the two edges in apposition for convenient application of a clip or other connector. Because the required manipulation is simple, a single surgeon may perform the anastomosis, and can coordinate manipulation of the everting and clipping tools in the process. Once a first suture, staple or clip has been applied, the eversion tends to remain stable, and the tool can be withdrawn while the remaining clips or sutures are applied.

While the preceding paragraphs describe an anastomosis, it should be understood that the tool is not limited to such uses. In fact, the tool has also proven particularly useful for effecting skin closures, using sutures or staples to join the approximated edges of the skin. This is particularly relevant in skin closures by staples where assistance ordinarily is necessary to maintain skin eversion, since the instrument eliminates the need for an assistant.

A second embodiment of the invention is shown in FIG. 7. In the second embodiment, wherein identical parts are designated by numerals identical to those of FIG. 1, and modified parts are indicated by numerals differing by one hundred from those in FIG. 1, the tool is of a unitary molded construction, having a head 116 from which extend an upper leg 110 and lower portion 111 having a first relatively flexible portion 113 adjacent the head, a second relatively inflexible portion 115 near the middle of the tool said inflexible portion being bifurcated to form the intermediate and lower legs 112, 114. In this embodiment, the three legs are also interconnected by webs or fulcrums 117, 119 near the jawed ends, so that inward pressure on the legs produces outward movement of the jaws. It will be appreciated that the rest position of the jaws is closed, or nearly so, in this embodiment, and that the action of the tool is opposite that for the first-described embodiment, since pressure must be applied to release the tissues. This arrangement may be preferable in certain circumstances.

In the second embodiment, the three legs have tapered ends 28 with jaws 26, 32, 34 at the ends thereof like those of the first embodiment.

Other variations and modifications of the invention may occur to those of skill in the art. It is therefore intended that the foregoing be regarded as merely illustrative of the invention, which should be measured by the claims that follow.

I claim:
1. An everting forceps comprising
    a pair of outer resilient legs rigidly interconnected at one end thereof,
    a third leg intermediate said pair of legs,
    externally manipulable means for enabling one to move the intermediate leg with respect to one of the first and second legs by manually applying pressure thereto,
    said intermediate leg terminating at a tip provided with a spherical jaw, and each of said outer legs terminating at a tip provided with an acurate jaw, each of said acurate jaws being positioned and configurated to cooperate with said spherical jaw.
2. The invention of claim 1, wherein said arcuate jaws extend around a major portion of said spherical jaws.
3. The invention of claim 1, wherein said spherical jaw protrudes beyond the ends of said arcuate jaws.
4. The invention of claim 1, wherein each of said first and second jaws is made of a resilient material whereby the legs act as leg springs to bias said jaws apart.
5. The invention of claim 1, further comprising a first fulcrum connected between said first and intermediate legs proximate said jaws, and a second fulcrum connected between said intermediate and second legs proximate said jaws, whereby said jaws may be opened by applying inward pressure to said outer legs.
6. The invention of claim 5, wherein said arcuate jaws extend around a major portion of said spherical jaws.
7. The invention of claim 5, wherein said spherical jaw protrudes beyond the ends of said arcuate jaws.
8. The invention of claim 5, wherein each of said first, intermediate and second legs is made of a resilient material, whereby the legs act as leg springs to bias said jaws together.
9. An everting forceps comprising
    a pair of outer resilient legs rigidly interconnected at one end thereof,
    a third leg intermediate said pair of legs,
    said outer and intermediate legs having respective tips at their free ends, said tips being provided with respective jaws, and further comprising
    externally manipulable means for enabling one to move the intermediate leg with respect to one of the first and second legs by manually applying pressure thereto,
    a first fulcrum connected between said first and intermediate legs proximate said jaws, and a second fulcrum connected between said intermediate and second legs proximate said jaws, whereby said jaws may be opened by applying inward pressure to said outer legs,
    wherein said intermediate leg and one of said outer legs are integrally connected by a relatively inflexible portion which in turn is connected to said head by a relatively flexible portion.

* * * * *